United States Patent
Choi et al.

(10) Patent No.: US 12,338,426 B2
(45) Date of Patent: Jun. 24, 2025

(54) CELL STIMULATION APPARATUS, AND ULTRASONIC AND ELECTRICAL STIMULATION APPARATUS

(71) Applicant: DAEGU GYEONGBUK INSTITUTE OF SCIENCE AND TECHNOLOGY, Daegu (KR)

(72) Inventors: Hong Soo Choi, Daegu (KR); Eun Jung Shin, Daegu (KR); Hong Goo Yeo, Daejeon (KR); Eun Hee Kim, Goyang-si (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 414 days.

(21) Appl. No.: 17/284,108

(22) PCT Filed: Oct. 7, 2019

(86) PCT No.: PCT/KR2019/013104
§ 371 (c)(1),
(2) Date: Apr. 9, 2021

(87) PCT Pub. No.: WO2020/116765
PCT Pub. Date: Jun. 11, 2020

(65) Prior Publication Data
US 2021/0348108 A1    Nov. 11, 2021

(30) Foreign Application Priority Data
Dec. 3, 2018 (KR) .......................... 10-2018-0153712

(51) Int. Cl.
*C12M 1/42* (2006.01)
*C12M 1/34* (2006.01)

(52) U.S. Cl.
CPC ............ *C12M 35/02* (2013.01); *C12M 35/04* (2013.01); *C12M 41/46* (2013.01)

(58) Field of Classification Search
CPC ...... C12M 35/02; C12M 35/04; C12M 41/46; C12M 1/42
See application file for complete search history.

(56) References Cited

U.S. PATENT DOCUMENTS

| 5,134,070 A * | 7/1992 | Casnig .................... C12M 23/10 435/173.6 |
| 2010/0159580 A1* | 6/2010 | Kim ....................... C12M 35/04 435/297.1 |

FOREIGN PATENT DOCUMENTS

| DE | 102010052197 A1 * | 5/2012 | ............ C12M 23/12 |
| JP | 2008520199 | 6/2008 | |

(Continued)

OTHER PUBLICATIONS

Lee, W., et al., "All-in-one low-intensity pulsed ultrasound stimulation system using piezoelectric micromachined ultrasonic transducer (pMUT) arrays for targeted cell stimulation", Sep. 19, 2017, Biomed Microdevices (2017) 19:86, pp. 1-9. (Year: 2017).*

(Continued)

*Primary Examiner* — Jonathan M Hurst
(74) *Attorney, Agent, or Firm* — LEX IP MEISTER, PLLC

(57) ABSTRACT

A cell stimulation apparatus according to an embodiment of the present invention includes: an electrode unit in which an electrode element is installed; a pMUT element disposed above the electrode unit to be spaced apart from the electrode unit, and configured to generate an ultrasonic wave through a voltage applied thereto; and a well element installed between the electrode unit and the pMUT element and forming a cell chamber together with the electrode unit and the pMUT element, wherein a bio-sample is disposed on (Continued)

the electrode element, and the ultrasonic wave generated by the pMUT element is transmitted to the bio-sample so as to provide ultrasound stimulation to the bio-sample.

10 Claims, 7 Drawing Sheets

(56) References Cited

FOREIGN PATENT DOCUMENTS

| | | |
|---|---|---|
| JP | 2011172545 | 9/2011 |
| JP | 2013255483 | 12/2013 |
| JP | 2016503312 | 2/2016 |
| KR | 10-2013-0037468 | 4/2013 |
| KR | 10-2015-0125350 | 11/2015 |

OTHER PUBLICATIONS

Choe, Hong-Su et al., "Fabrication and application of piezoelectric material by microprocessing technology", Ceramist 2014;17(2):48-59. Published online Jun. 30, 2014.

* cited by examiner

CELL STIMULATION APPARATUS, AND ULTRASONIC AND ELECTRICAL STIMULATION APPARATUS

TECHNICAL FIELD

The present invention relates to a cell stimulation apparatus and an ultrasound and electric stimulation apparatus.

BACKGROUND ART

In general, cells in mechano-responsive tissue of humans and animals are exposed to various types of mechanical stimulation including a tensile force, a shear force, a compression force, etc. Thus, when articular cartilage tissue is exposed to repeated mechanical stimulation, a disease like arthritis can be caused. Accordingly, research into cellular responses induced by mechanical stimulation has been receiving attention.

In order to produce a stem cell that can differentiate into replacement tissue for humans and animals and, in particular, into mechano-responsive tissue with full functionality, it is required to apply mechanical stimulation to the stem cell while the stem cell is cultured. Here, the degree of the stimulation applied to the stem cell varies depending on the type of the cell and the kind of tissue to be obtained.

Research has been conducted on the cellular response and on the stimulation of cells for stem cell differentiation. For example, Korean Patent Application Publication no. 10-2012-0139399 discloses an ultrasonic-stimulated perfusion flow bioreactor system for culturing adult stem cells, and Korean Patent Application Publication no. 10-2009-0008784 discloses a method of efficiently isolating and culturing mesenchymal stem cells from human tissues and their cells by using low-intensity ultrasound.

DISCLOSURE OF INVENTION

Technical Problem

The objective of the present invention according to an embodiment is to provide a cell stimulation apparatus and an ultrasound and electric stimulation apparatus, capable of preventing an attenuation of ultrasonic waves transmitted to a stimulation target and accurately transmitting ultrasound stimulation and electrical stimulation to the stimulation target.

Solution to Problem

A cell stimulation apparatus according to an embodiment of the present invention may include: an electrode unit in which an electrode element is installed; a pMUT element disposed above the electrode unit to be spaced apart from the electrode unit, and configured to generate an ultrasonic wave through a voltage applied thereto; and a well element installed between the electrode unit and the pMUT element and forming a cell chamber together with the electrode unit and the pMUT element, wherein a bio-sample is disposed on the electrode element, and the ultrasonic wave generated by the pMUT element is transmitted to the bio-sample so as to provide ultrasound stimulation to the bio-sample.

The electrode element may provide the bio-sample with electric stimulation, and may detect a signal that is generated in the bio-sample by the ultrasound stimulation or the electric stimulation.

The electrode element may be provided as a plurality of electrode elements, and the pMUT element may be provided as a plurality of pMUT elements so as to correspond to the plurality of electrode elements.

The plurality of electrode elements and the plurality of pMUT elements may be provided, respectively, in the form of an array.

A plurality of bio-samples may be disposed, respectively, on the plurality of electrode elements, such that the ultrasound stimulation or the electric stimulation is provided individually to the plurality of bio-samples by the plurality of electrode elements and the plurality of pMUT elements.

An insulation material may be applied to a surface of the pMUT element.

An ultrasound and electric stimulation apparatus according to an embodiment of the present invention may include: an ultrasound stimulation unit configured to transmit ultrasound stimulation to a stimulation target; an electric stimulation unit disposed below the ultrasound stimulation unit to be spaced apart from the ultrasound stimulation unit, and configured to transmit electric stimulation to the stimulation target, wherein the stimulation target may be disposed between the ultrasound stimulation unit and the electric stimulation unit; and a well element disposed between the ultrasound stimulation unit and the electric stimulation unit and forming, together with the ultrasound stimulation unit and the electric stimulation unit, a cell chamber in which the stimulation target is received.

The electric stimulation unit may detect a signal that is generated in the stimulation target by the ultrasound stimulation or the electric stimulation.

An insulation material may be applied to a surface of the ultrasound stimulation unit.

A pMUT element or a pMUT array may be provided as the ultrasound stimulation unit, and an electrode element or a multi-electrode array (MEA) may be provided as the electric stimulation unit.

Advantageous Effects of Invention

The cell stimulation apparatus and the ultrasound and electric stimulation apparatus according to embodiments of the present invention are characterized in that the ultrasound stimulation unit (or the pMUT element) and the electric stimulation unit (or the electrode unit) are spaced apart from each other by a predetermined distance by the well element, such that the ultrasound stimulation is directly transmitted from the ultrasound stimulation unit to the stimulation target.

In addition, as the ultrasound stimulation is directly transmitted from the ultrasound stimulation unit to the stimulation target, the ultrasonic wave may be prevented from attenuating as compared to when the ultrasound stimulation is transmitted to the stimulation target via the electric stimulation unit, and the ultrasound stimulation may be accurately transmitted to the stimulation target.

Furthermore, the ultrasound stimulation may be provided to or received from the stimulation target through the ultrasound stimulation unit (the pMUT element).

Moreover, in a case where the ultrasound stimulation unit (or the pMUT element) is provided in the form of an array, various experiments may be rapidly performed for at least one stimulation target.

In addition, the pMUT element (or the ultrasound stimulation unit) may be manufactured in various sizes and designs, by using an MEMS process.

The effects of the cell stimulation apparatus and the ultrasound and electric stimulation apparatus according to the embodiments of the present invention are not limited to the above-mentioned effects, and other effects that are not mentioned above will be more clearly understood by a person skilled in the art from the following description.

BRIEF DESCRIPTION OF DRAWINGS

The foregoing and other objects, features, and advantages of the invention, as well as the following detailed description of the embodiments, will be better understood when read in conjunction with the accompanying drawings. For the purpose of illustrating the invention, there is shown in the drawings an exemplary embodiment that is presently preferred, it being understood, however, that the invention is not intended to be limited to the details shown because various modifications and structural changes may be made therein without departing from the spirit of the invention and within the scope and range of equivalents of the claims. The use of the same reference numerals or symbols in different drawings indicates similar or identical items.

DESCRIPTION OF EMBODIMENTS

Figure 1:
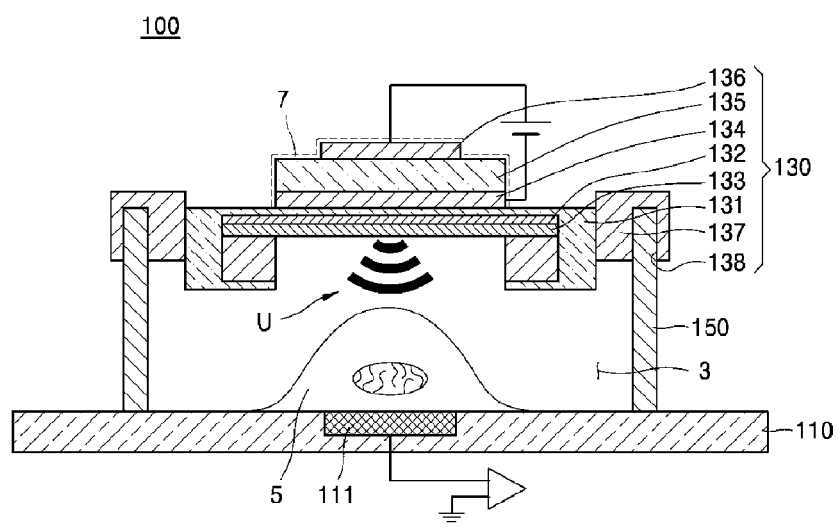
FIG. 1 is a front cross-sectional view of a cell stimulation apparatus according to an embodiment of the present invention.
Figure 2:
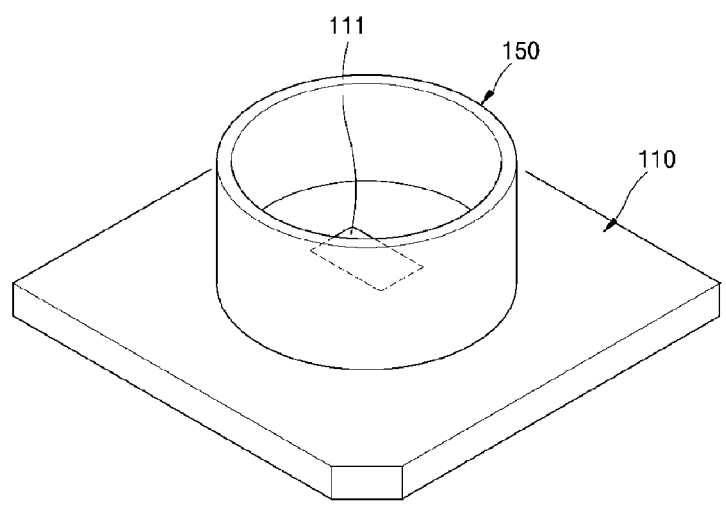
FIG. 2 illustrates a state in which a well element and an electrode unit are coupled to each other according to an embodiment of the present invention.

Hereinafter, embodiments of the present invention will be described in detail referring to exemplary drawings. It is to be noted that like reference numerals designate like elements throughout the drawings. In describing the embodiments, when it is determined that the detailed description of the relevant known technology or function unnecessarily obscures the gist of the embodiments, the detailed description will be omitted.

When the terms "first," "second," "A," "B," "(a)," "(b)," etc. are used herein to describe various elements of the embodiments, these terms are merely used to distinguish the elements from each other, and do not limit a sequence or order of the elements unless clearly indicated by the context. When an element or layer is referred to as being "engaged to," "connected to," or "coupled to" another element or layer, it means that the element or layer is directly engaged, connected or coupled to the another element or layer, and it is to be noted that there could be an intervening element or layer therebetween.

Like reference numerals indicate like elements throughout the embodiments. Unless described otherwise, description in one embodiment can be applied to another embodiment, and overlapping description will be omitted.

Referring to FIGS. 1 to 5, a cell stimulation apparatus 100 according to an embodiment may include an electrode unit 110, a pMUT element 130, and a well element 150.

An electrode element 111 may be installed in the electrode unit 110, and specifically, a plurality of electrode elements 111 may be installed on a substrate of the electrode unit 110. The plurality of electrode elements 111 may be provided in the form of an array. The plurality of electrode elements 111 in the form of an array may be provided as a multi-electrode array (MEA). The plurality of electrode elements 111 may be disposed to be spaced apart from each other, and may be disposed at positions corresponding to a plurality of pMUT elements 130, respectively, to face the plurality of pMUT elements 130 (which will be described below).

Each of the plurality of electrode elements 111 may have a planar shape. The plurality of electrode elements 111 may transmit electric stimulation generated therein to a bio-sample 5. The same bio-sample 5 or different bio-samples 5 may be disposed on the plurality of electrode elements 111 (see FIG. 5). Accordingly, referring to FIG. 5, a bio-sample 5 among the bio-samples 5 that are disposed on the plurality of electrode elements 111 may be provided with ultrasound stimulation by a pMUT element 130 that is disposed directly above the bio-sample 5, and then an electrode element 111 directly under the bio-sample 5 may detect a signal generated in the bio-sample 5. When another bio-sample 5 among the bio-samples 5 disposed on the plurality of electrode elements 111 is provided with electric stimulation by an electrode element 111 directly under the bio-sample 5, the electrode element 111 may detect a signal generated in the bio-sample 5. When still another bio-sample 5 among the bio-samples 5 disposed on the plurality of electrode elements 111 is provided with ultrasound stimulation by a pMUT element 130 that is disposed directly above the bio-sample 5 and with electric stimulation by an electrode element 111 directly under the bio-sample 5 at the same time, the electrode element 111 may detect a signal generated in the bio-sample 5.

"U" in FIGS. 1 to 7 refers to the ultrasound stimulation.

As the plurality of pMUT elements 130 and the plurality of electrode elements 111 provide, respectively, the ultrasound stimulation and the electric stimulation to the same or different bio-samples 5, the cell stimulation apparatus 100 may have an effect of allowing various experiments to be rapidly performed.

The electrode element 111 may be made of a metal thin film comprising gold, platinum, etc., and may have a planar shape.

The bio-sample 5 may be disposed on the electrode unit 110, and specifically, may be disposed on the electrode element 111. The electrode element 111 may provide the bio-sample 5 with the electric stimulation by using a voltage applied to the electrode element 111. The electrode unit 110 may detect a signal that is generated in the bio-sample 5 when the ultrasound stimulation is transmitted to the bio-sample 5 by the pMUT element 130 (which will be described in detail below) or when the electric stimulation is transmitted to the bio-sample 5 by the electrode element 111. Here, the signal detected in the bio-sample 5 may indicate a change in the bio-sample 5 occurring due to the ultrasound stimulation or the electric stimulation.

Although not specifically illustrated, at least one voltage application apparatus (not illustrated) may be connected to the electrode unit 110. Both of the pMUT element 130 (which will be described in detail below) and the electrode unit 110 may be connected to a single voltage application apparatus. Alternatively, the pMUT element 130 may be connected to a voltage application apparatus, and the electrode unit 110 may be connected to another voltage application apparatus. However, the present invention is not limited thereto, and various modifications and variations can be made.

The electrode unit 110 of the cell stimulation apparatus 100 may be manufactured in various sizes and designs through a micro-electro mechanical systems (MEMS) process.

Referring to FIG. 1, the pMUT element 130 may be disposed above the electrode unit 110, and may generate an ultrasonic wave by using a voltage applied thereto. The pMUT element 130 may be a type of ultrasonic transducer capable of generating an ultrasonic wave by using a voltage applied thereto, and may be manufactured through the MEMS process.

The pMUT element 130 may include a mask 131, a substrate portion 132, a silicon oxide 133, a lower electrode 134, a piezoelectric material 135, an upper electrode 136, and a cover portion 137.

Figure 5:
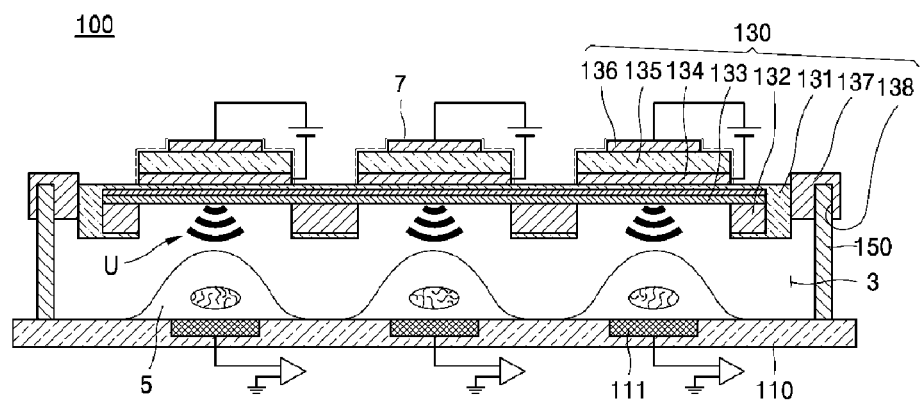
FIG. 5 illustrates a cell stimulation apparatus being used according to an embodiment of the present invention.

The pMUT element 130 may have a planar shape, and when a voltage is applied to the pMUT element 130, an ultrasonic wave in the form of a plane wave may be transmitted to the bio-sample 5 disposed below the pMUT element 130 (see FIG. 5). Therefore, the cell stimulation apparatus 100 may provide ultrasound stimulation, physical stimulation, or mechanical stimulation to the bio-sample 5 disposed on the electrode element 111 or, specifically, to biological tissues and cells including neurons and brain slices.

The pMUT element 130 may be coupled to the well element 150 (which will be described in detail below), and specifically, one side of the pMUT element 130 (a lower side of the pMUT element 130 in FIG. 3) may be fixedly coupled to one side of the well element 150 (an upper side of the well element 150 in FIG. 3) while covering the one side of the well element 150. Therefore, the pMUT element 130 may be disposed to be spaced apart from the electrode unit 110, that is, may be disposed to be spaced apart from the electrode element 111, and may directly transmit the ultrasound stimulation to the bio-sample 5 disposed on the electrode element 111 (see FIG. 3). In addition, as the ultrasound stimulation generated by the pMUT element 130 is directly transmitted to the bio-sample 5 without passing through the electrode unit 110 or the like, an attenuation of ultrasonic wave may be prevented, and the ultrasound stimulation may be accurately transmitted to the bio-sample 5.

The pMUT element 130 may be provided as a plurality of pMUT elements 130, and the plurality of pMUT elements 130 may be provided in the form of an array. Each of the plurality of pMUT elements 130 may have a planar shape, and ultrasonic waves generated by the plurality of pMUT elements 130 may be transmitted in the form of a plane wave to the bio-samples 5 disposed on the plurality of the electrode elements 111 (see FIG. 5).

In the present specification, providing the plurality of pMUT elements 130 means that a coupling body of the lower electrode 134, the piezoelectric material 135, and the upper electrode 136, which is coupled to the substrate portion 132 and the silicon oxide 133, is provided as a plurality of coupling bodies.

In the pMUT element 130, the silicon oxide 133 may be formed on an upper surface of the substrate portion 132 (see FIG. 3), to thereby form, for example, a silicon-on-insulator (SOI) wafer. The mask 131 for etching may be coupled to the substrate portion 132, covering an outer side of the substrate portion 132. Then, the plurality of coupling bodies of the lower electrode 134, the piezoelectric material 135, and the upper electrode 136 may be provided on the upper surface of the substrate portion 132 to which the silicon oxide 133 is coupled, such that a pMUT array is formed.

The lower electrode 134 may be deposited on an upper side of the silicon oxide 133, and then the piezoelectric material 135 may be deposited on an upper surface of the lower electrode 134. Then, the upper electrode 136 may be deposited on an upper surface of the piezoelectric material 135.

An insulation material 7 may be applied to a surface of the pMUT element 130 so as to cover the pMUT element 130, that is, so as to cover all of the mask 131, the substrate portion 132, the silicon oxide 133, the lower electrode 134, the piezoelectric material 135, and the upper electrode 136. The insulation material 7 may be made of a water-proof material.

The pMUT element 130 of the cell stimulation apparatus 100 may be manufactured in various sizes and designs through the MEMS process.

The well element 150 may be installed between the electrode unit 110 and the pMUT element 130, and may form a cell chamber 3 together with the electrode unit 110 and the pMUT element 130.

The well element 150 may be formed in a shape of which an upper portion and a lower portion are open (see FIG. 1). In the present embodiment, the well element 150 is formed in a cylindrical shape of which an upper portion and a lower portion are open, but the present invention is not limited thereto, and various modifications can be made. For example, the well element 150 may be formed in the shape of a rectangular parallelepiped, a regular hexahedron, or the like, of which an upper portion and a lower portion are open.

Figure 3:
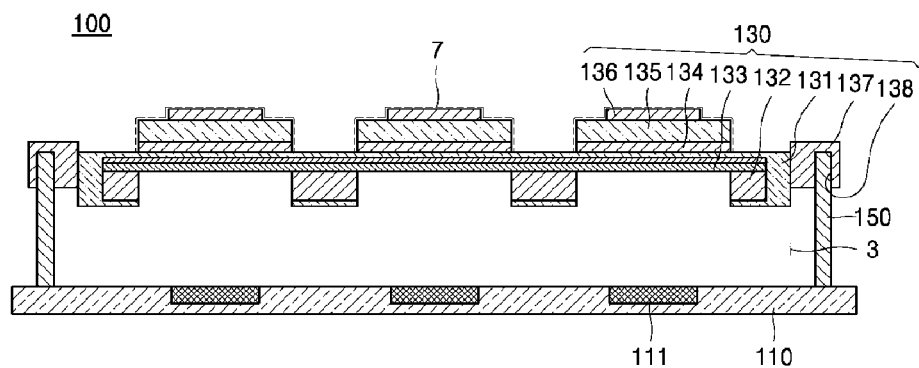
FIG. 3 is a front cross-sectional view of a cell stimulation apparatus according to an embodiment of the present invention.
Figure 4:
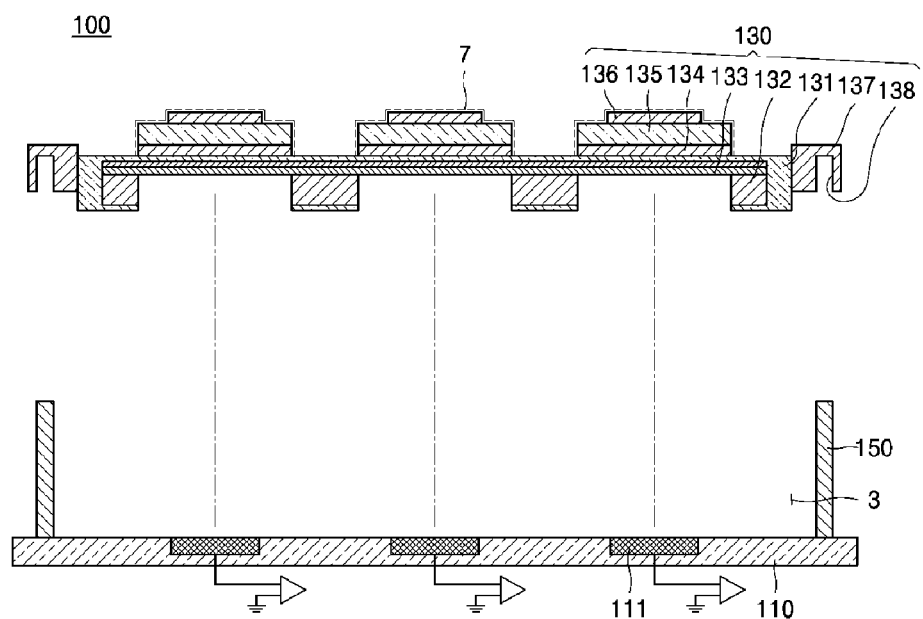
FIG. 4 is a front cross-sectional view of a cell stimulation apparatus in a disassembled state according to an embodiment of the present invention.

A lower end portion of the well element 150 may be fixedly coupled to the electrode unit 110, and an upper end portion of the well element 150 may be fixedly coupled to the pMUT element 130 (see FIG. 3). When the lower end portion of the well element 150 is fixedly coupled to the electrode unit 110, the bio-sample 5 may be injected through the upper portion of the well element 150 (see FIG. 4). Here, the bio-sample 5 may be cultured inside the well element 150.

A cover groove 138 formed in a cover portion 137 of the pMUT element 130 may be formed in a shape corresponding to the upper end portion of the well element 150. As the pMUT element 130 covers the well element 150, the pMUT element 130 and the electrode element 111 may be fixed at such positions that the pMUT element 130 and the electrode element 111 face each other. In addition, the well element 150 according to an embodiment of the present invention may enable the bio-sample 5 to be disposed on the electrode element 111 and to be maintained in a stable state such that the ultrasound stimulation or the electric stimulation is accurately transmitted to the bio-s ample 5. The pMUT element 130 and the electrode element 111 may be disposed to be spaced apart from each other by a predetermined distance by the well element 150. Accordingly, the ultrasound stimulation may be transmitted from the pMUT element 130 directly to the bio-sample 5 disposed on the electrode element 111, without passing through the electrode element 111. In addition, as the ultrasound stimulation is transmitted from the pMUT element 130 directly to the bio-sample 5 without passing through the electrode element 111, the ultrasonic wave may be prevented from attenuating.

As the well element 150 is present, the ultrasound stimulation may be transmitted from the pMUT element 130 directly to the bio-sample 5 disposed on the electrode element 111, and the electric stimulation may be transmitted to the bio-sample 5 from the electrode element 111. Accordingly, the cell stimulation apparatus 100 may be operated such that the ultrasound stimulation and the electric stimulation are individually transmitted. In addition, as the well element 150 is present, the pMUT element 130 may be spaced apart from the electrode unit 110, that is, from the electrode element 111, and thus, the ultrasound stimulation may be accurately transmitted from pMUT element 130 to the bio-sample 5 without the insulation material 7 which is required to reduce an attenuation of ultrasonic wave in a structure where the pMUT element 130 and the electrode element 111 are sequentially stacked.

Hereinbelow, the operation principle and effect of the cell stimulation apparatus 100 will be described.

The cell stimulation apparatus 100 may include the electrode unit 110, the pMUT element 130, and the well element 150.

The well element 150 may be installed between the electrode unit 110 and the pMUT element 130, and may be formed in a shape of which the upper portion and the lower portion are open (see FIG. 3). The lower end portion of the well element 150 may be coupled to the upper surface of the electrode unit 110 (see FIG. 3), and the upper end portion of the well element 150 may be covered by the pMUT element 130.

A plurality of electrode elements 111 may be formed in the electrode unit 110, and a coupling body of the lower electrode 134, the piezoelectric material 135, and the upper electrode 136 of the pMUT element 130 may be provided as a plurality of coupling bodies, wherein the plurality of coupling bodies may face the plurality of electrode elements 111.

As the well element 150 is installed between the electrode unit 110 and the pMUT element 130, the pMUT element 130 may be spaced apart from the electrode unit 110, and the bio-sample 5 may be disposed between the electrode unit 110 and the pMUT element 130. Specifically, the bio-sample 5 may be disposed below the pMUT element 130 and on the upper surface of the electrode element 111 installed in the electrode unit 110. Accordingly, the ultrasound stimulation generated by the pMUT element 130 may be transmitted directly to the bio-sample 5. Therefore, the ultrasound stimulation may be transmitted directly to the bio-sample 5 without passing through the electrode unit 110 or the like, and thus the ultrasonic wave may be prevented from attenuating. If the pMUT element 130 and the electrode unit 110 are sequentially stacked, the insulation material 7 may be required to be installed between the pMUT element 130 and the electrode unit 110 for individual driving of the pMUT element 130 and the electrode unit 110. In contrast, in the cell stimulation apparatus 100 of the present invention, the pMUT element 130 may be disposed to be spaced apart from the electrode unit 110 by a predetermined distance by the well element 150. Accordingly, the ultrasound stimulation generated by the pMUT element 130 may be transmitted directly to the bio-sample 5, and the electric stimulation of the electrode unit 110 may be independently transmitted to the bio-sample 5 without contacting the pMUT element 130. In other words, the cell stimulation apparatus 100 of the present invention may have effects of providing the ultrasound stimulation and the electric stimulation to the bio-sample 5 independently, and providing the ultrasound stimulation and the electric stimulation simultaneously or sequentially.

In addition, the electrode element 111 may detect a signal that is generated in the bio-sample 5 by the ultrasound stimulation or the electric stimulation. Specifically, the electrode element 111 may detect a signal that is generated in the bio-sample 5 when the ultrasound stimulation is provided to the bio-sample 5, when the electric stimulation is provided to the bio-sample 5, and when the ultrasound stimulation and the electric stimulation are provided to the bio-sample 5 at the same time. Furthermore, the pMUT element 130 may provide the bio-sample 5 with the ultrasound stimulation, and the electrode unit 110, that is, the electrode element 111, may detect the signal generated in the bio-sample 5. Therefore, transmission of the ultrasound stimulation to the bio-sample 5 and detection of the signal generated in the bio-sample 5 may be performed simultaneously. In addition, after the electrode element 111 provides the bio-sample 5 with the electric stimulation, the electrode element 111 may detect the signal generated in the bio-sample 5.

Hereinbelow, the configuration, operation principle, and effect of an ultrasound and electric stimulation apparatus 200 will be described.

Figure 6:
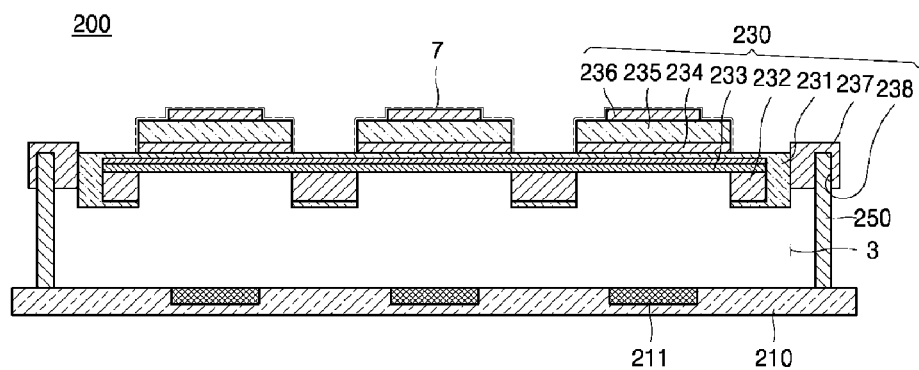
FIG. 6 is a front cross-sectional view of an ultrasound and electric stimulation apparatus according to an embodiment of the present invention.
Figure 7:
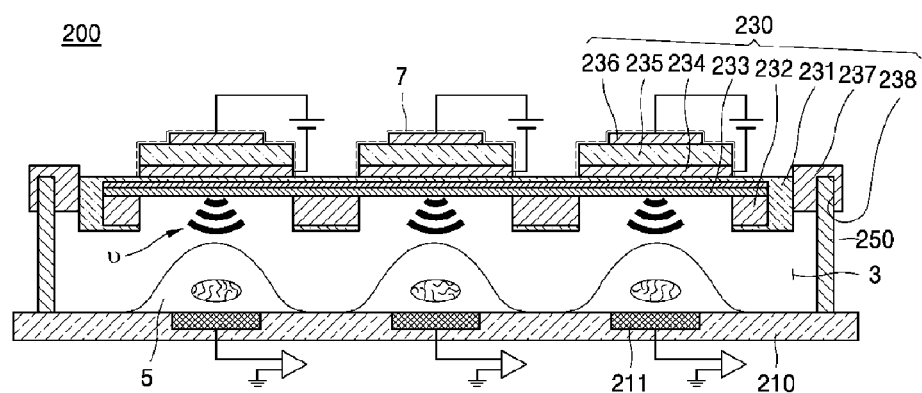
FIG. 7 illustrates an ultrasound and electric stimulation apparatus being used according to an embodiment of the present invention.

Referring to FIGS. 6 and 7, the ultrasound and electric stimulation apparatus 200 may include an electric stimulation unit 210, an ultrasound stimulation unit 230, and a well element 250.

The electric stimulation unit 210 may be disposed below the ultrasound stimulation unit 230 to be spaced apart from the ultrasound stimulation unit 230, and may transmit electric stimulation to a stimulation target 5. The ultrasound stimulation unit 230 may be disposed above the electric stimulation unit 210 (see FIG. 6) and transmit ultrasound stimulation to the stimulation target 5. Here, the stimulation target 5 may be anything that requires ultrasound stimulation or electric stimulation, and the ultrasound and electric stimulation apparatus 200 may be configured as a medical apparatus or the like.

The ultrasound stimulation unit 230 may be provided as a pMUT element or a pMUT array, and the electric stimulation unit 210 may be provided as an electrode element 211 or an MEA.

The ultrasound stimulation unit 230 may include a mask 231, a substrate portion 232, a silicon oxide 233, a lower electrode 234, a piezoelectric material 235, an upper electrode 236, and a cover portion 237. A cover groove 238 may be formed in the cover portion 347 in a shape corresponding to the shape of the well element 250, such that the well element 250 is inserted into the cover groove 238. As a result, the well element 250 may be stably coupled to the ultrasound stimulation unit 230. In addition, an insulation material 7 made of a water-proof material may be applied to a surface of the ultrasound stimulation unit 230.

The well element 250 may be disposed between the ultrasound stimulation unit 230 and the electric stimulation unit 210, and may form a cell chamber 3 together with the ultrasound stimulation unit 230 and the electric stimulation unit 210.

The stimulation target 5 disposed on the electric stimulation unit 210, that is, on the electrode element 211 (see FIG. 6), may be received inside the cell chamber 3, which is a space formed and surrounded by the ultrasound stimulation unit 230, the electric stimulation unit 210, and the well element 250.

As the well element 250 is provided, the ultrasound stimulation unit 230 and the electric stimulation unit 210 are not stacked but may be disposed to be spaced apart from each other by a predetermined distance. Accordingly, the ultrasound stimulation generated by the ultrasound stimulation unit 230 may be transmitted directly to the stimulation target 5 without passing through the electric stimulation unit 210. In addition, as the ultrasound stimulation is transmitted directly to the stimulation target 5, the ultrasonic wave may be prevented from attenuating, and the ultrasound stimulation may be accurately transmitted. If the ultrasound stimulation unit 230 and the electric stimulation unit 210 are sequentially stacked, the insulation material 7 is required to be installed between the ultrasound stimulation unit 230 and the electric stimulation unit 210. In contrast, as the well element 150 is present between the ultrasound stimulation unit 230 and the electric stimulation unit 210 in the present invention, the insulation material 7 is not required to be installed between the ultrasound stimulation unit 230 and the electric stimulation unit 210, and the ultrasound stimulation unit 230 and the electric stimulation unit 210 may be independently driven.

In detail, the ultrasound stimulation generated by the ultrasound stimulation unit 230 may be transmitted to the stimulation target 5, and the electric stimulation unit 210 may provide the electric stimulation to the stimulation target 5 or detect a signal generated in the stimulation target 5.

While the present invention has been explained in relation to its embodiments and drawings, it is to be understood from the description above by a person skilled in the art that various modifications and variations thereof can be made. For example, an appropriate result can be achieved even when the present invention is carried out in a different order from the order described in the detailed description, and/or even when the components including systems, structures, apparatuses, circuits, etc. are coupled or combined in a different way from the way described in the detailed description, or replaced or substituted by other components or equivalents.

The invention claimed is:

1. A cell stimulation apparatus comprising:
    an electrode unit in which an electrode element is installed and exposed as a portion of a top surface of the electrode unit, and configured to transmit electric stimulation;
    a piezoelectric micromachined ultrasonic transducer (pMUT) element disposed above the electrode unit to be spaced apart from the electrode unit, and configured to generate an ultrasonic wave through a voltage applied thereto; and
    a well element installed between the electrode unit and the pMUT element and forming a cell chamber together with the electrode unit and the pMUT element,
    wherein the cell chamber is a closed space enclosed by the well element, the electrode unit, and the pMUT element, and
    wherein a bio-sample is disposed directly on and directly contacts the electrode element, and receives the electric stimulation from the electrode element, and
    wherein the ultrasonic wave generated by the pMUT element is transmitted to the bio-sample so as to provide ultrasound stimulation to the bio-sample located in the cell chamber.

2. The cell stimulation apparatus of claim 1, wherein the electrode element provides the bio-sample with electric stimulation, and detects a signal that is generated in the bio-sample by the ultrasound stimulation or the electric stimulation.

3. The cell stimulation apparatus of claim 2, wherein the electrode element is provided as a plurality of electrode elements, and the pMUT element is provided as a plurality of pMUT elements so as to correspond to the plurality of electrode elements.

4. The cell stimulation apparatus of claim 3, wherein the plurality of electrode elements and the plurality of pMUT elements are provided, respectively, in the form of an array.

5. The cell stimulation apparatus of claim 4, wherein a plurality of bio-samples are disposed, respectively, on the plurality of electrode elements, such that the ultrasound stimulation or the electric stimulation is provided to the plurality of bio-samples individually by the plurality of electrode elements and the plurality of pMUT elements.

6. The cell stimulation apparatus of claim 1, wherein an insulation material is applied to a surface of the pMUT element.

7. An ultrasound and electric stimulation apparatus comprising:
    an ultrasound stimulation unit configured to transmit ultrasound stimulation to a stimulation target;
    an electric stimulation unit disposed below the ultrasound stimulation unit to be spaced apart from the ultrasound stimulation unit, and configured to transmit electric stimulation to the stimulation target, wherein the stimulation target is disposed between the ultrasound stimulation unit and the electric stimulation unit; and
    a well element disposed between the ultrasound stimulation unit and the electric stimulation unit and forming, together with the ultrasound stimulation unit and the electric stimulation unit, a cell chamber in which the stimulation target is received,
    wherein the electric stimulation unit includes an electrode element exposed as a portion of a top surface of the electric stimulation unit, and configured to transmit the electric stimulation,
    wherein the stimulation target is disposed directly on and directly contacts the electrode element, and receives the electric stimulation from the electrode element, and
    wherein the cell chamber is a closed space enclosed by the well element, the ultrasound stimulation unit and the electric stimulation unit, and
    wherein the ultrasound stimulation unit and the electric stimulation unit provide stimulation on the stimulation target located in the cell chamber.

8. The ultrasound and electric stimulation apparatus of claim 7, wherein the electric stimulation unit detects a signal that is generated in the stimulation target by the ultrasound stimulation or the electric stimulation.

9. The ultrasound and electric stimulation apparatus of claim 7, wherein an insulation material is applied to a surface of the ultrasound stimulation unit.

10. The ultrasound and electric stimulation apparatus of claim 7, wherein the ultrasound stimulation unit is provided as a pMUT element or a pMUT array, and the electric stimulation unit is provided as an electrode element or a multi-electrode array (MEA).

* * * * *